United States Patent [19]

Grafen et al.

[11] 4,206,153
[45] Jun. 3, 1980

[54] TREATMENT OF METHANOLIC-AQUEOUS RESIDUES FROM SYNTHESES EMPLOYING TRIPHENYLPHOSPHONIUM SALTS

[75] Inventors: Paul Grafen; Hans-Ulrich Scholz, both of Weisenheim; Bernhard Schulz, Schwetzingen, all of Fed. Rep. of Germany

[73] Assignee: BASF Aktiengesellschaft, Fed. Rep. of Germany

[21] Appl. No.: 969,665

[22] Filed: Dec. 15, 1978

[30] Foreign Application Priority Data

Dec. 17, 1977 [DE] Fed. Rep. of Germany ....... 2756321

[51] Int. Cl.$^2$ ............................................... C07F 9/53
[52] U.S. Cl. ..................................................... 568/14
[58] Field of Search .................... 260/606.5 P, 606.5 F

[56] References Cited

U.S. PATENT DOCUMENTS

| | | | |
|---|---|---|---|
| 2,879,303 | 3/1959 | Isler et al. | 260/606.5 P X |
| 2,879,304 | 3/1959 | Isler et al. | 260/606.5 P X |
| 2,945,069 | 7/1960 | Stern | 260/606.5 F |
| 2,983,739 | 5/1961 | Pommer et al. | 260/606.5 P X |
| 3,015,680 | 1/1962 | Isler et al. | 260/606.5 P X |
| 3,311,656 | 3/1967 | Surmatis | 260/606.5 P X |
| 3,347,932 | 10/1967 | Chechak | 260/606.5 F |
| 3,408,414 | 10/1968 | Surmatis | 260/606.5 F X |
| 3,468,931 | 9/1969 | Franceschi et al. | 260/606.5 F X |
| 3,600,473 | 8/1971 | Surmatis | 260/606.5 P X |
| 3,622,633 | 11/1971 | Surmatis | 260/606.5 F |
| 3,975,445 | 8/1976 | Kienzle et al. | 260/606.5 P X |

*Primary Examiner*—Helen M. S. Sneed
*Attorney, Agent, or Firm*—Keil & Witherspoon

[57] ABSTRACT

A process for treating residues which result from the Wittig synthesis of olefins and which consist principally of methanol, triphenylphosphine oxide, salts and organic by-products, by steam-stripping the volatile constituents, with partial condensation of the steam, and separating the resulting aqueous-organic mixture at 80°–100° C. into a saline aqueous phase and an organic phase containing principally triphenylphosphine oxide. Using this process provides a simple method of freeing, from triphenylphosphine oxide and other organic impurities, the effluent from syntheses which result in the formation of triphenylphosphine oxide, and thereby on the one hand substantially facilitates the purification of the effluent and on the other hand provides a simple method of recovering the triphenylphosphine oxide. The latter compound, which is easily purified by distillation or recrystallization, can then be used, for example, to prepare the triphenylphosphine required for Wittig syntheses or to prepare the triphenylphosphine dichloride required for the synthesis of pesticides.

1 Claim, No Drawings

TREATMENT OF METHANOLIC-AQUEOUS RESIDUES FROM SYNTHESES EMPLOYING TRIPHENYLPHOSPHONIUM SALTS

The present invention relates to a process for the treatment of residues consisting principally of methanol, triphenylphosphine oxide, salts and organic by-products, which residues are obtained, in the synthesis of olefins using triphenylphosphonium salts, after removal of the olefins.

In these syntheses which, like the Wittig synthesis, are employed industrially especially for the preparation of polyenes of the carotinoid series or their intermediates, the reaction mixtures first obtained essentially consist of an organic solvent and the products of the right-hand side of the following equation:

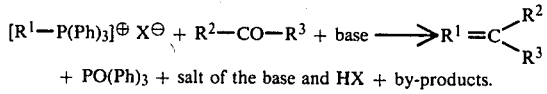

$+ PO(Ph)_3 +$ salt of the base and HX $+$ by-products.

In this equation, pH is phenyl, $X^\ominus$ is the acid equivalent of the phosphonium cation, $R^1$ is an ylid radical, in most cases an aliphatic or cycloaliphatic-aliphatic polyenyl group of 5 to 40, preferably of 5 to 20, carbon atoms, $R^2$ is an organic radical which is generally unsaturated and $R^3$ is hydrogen or also an organic radical. Depending on the nature of the base, the reaction mixture may also contain water if an aqueous base is used or if water is produced during the formation of the salt, for example if an alkali metal hydroxide is used. In the case of the industrial synthesis of vitamin A, the above organic radicals have the meaning shown in the following equation:

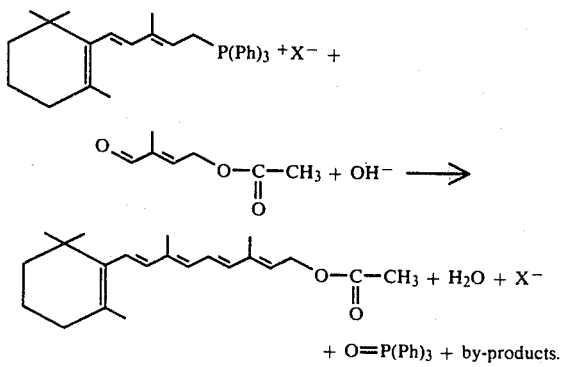

$+ O=P(Ph)_3 +$ by-products.

Other industrial syntheses of carotinoids, for example the oxidative dimerization of polyenyltriphenylphosphonium salts according to German Published Application DAS No. 2,505,869, also result in the formation of triphenylphosphine oxide and salts alongside the desired olefins, in accordance with the equation:

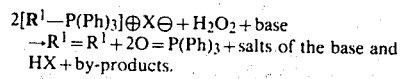

To isolate the desired product, ie. the olefin, pure or aqueous methanol is added to this primary mixture and the olefin is in general extracted from this mixture with a hydrophobic solvent, eg. heptane. Instead of isolating them by extraction, sparingly soluble carotinoids can also be isolated by filtration.

After this extraction or filtration, methanolic or aqueous-methanolic solutions are left, which principally contain triphenylphosphine oxide, the salt of the acid HX and the base used, any additional organic solvent and various organic by-products. These solutions can only be worked up with expensive equipment, since on evaporation of the mixtures the methanol, ie. the actual solvent for the triphenylphosphine oxide, distils off first. As a result, the triphenylphosphine oxide precipitates as an oil or as fine crystals in the aqueous salt phase. On further evaporation, the concentration of inorganic salts becomes so high, due to water partially distilling off, that the salts begin to precipitate. This clogs conventional evaporators very rapidly. The residue from such a difficult-to-operate distillation consists of a mixture of inorganic salts and crystalline triphenylphosphine oxide, with occluded by-products. In order to convert the triphenylphosphine oxide present in these residues into a form suitable for the regeneration of triphenylphosphine in accordance with German Pat. No. 1,247,310, German Pat. No. 1,192,205 or U.S. Pat. No. 3,847,999, expensive purification operations are needed. Combustion of the residue is expensive and troublesome because of the high proportion of inorganic salts.

It is an object of the present invention to treat the methanolic residues, resulting from the Wittig synthesis or from the oxidative dimerization of phosphonium salts, after extraction or isolation of the olefins, more economically than hitherto.

We have found that this object is achieved by a process for the treatment of residues, consisting principally of methanol, triphenylphosphine oxide, salts and organic by-products, from the synthesis of olefins using triphenylphosphonium salts, such as the residues obtained after separating off the olefin formed, wherein (a) these residues are steam-stripped at from 80° to 200° C. to remove the volatile constituents, principally methanol, (b) the steam treatment is carried out in such a way that at least sufficient water to keep the salts, contained in the residue, in solution can condense in the residue, (c) the aqueous organic mixture formed is transferred into a settling vessel, where it is kept at 80°–100° C. and (d) the phases which form in the vessel, namely a saline aqueous solution and an organic solution containing principally triphenylphosphine oxide, are separated from one another and processed further in the conventional manner.

The unexpected success of this process is based on the surprising discovery that under the stated conditions triphenylphosphine oxide is evidently converted by water into its hydrate, which melts below 100° C. and is an excellent solvent for organic substances. Accordingly, two liquid phases form, namely an aqueous phase which contains the greater part of the saline constituents, traces of methanol and very small amounts of organic substances, and a heavier organic phase which essentially consists of triphenylphosphine oxide hydrate and organic by-products which have formed during the olefin formation reaction.

According to our experience hitherto, the process is applicable to all syntheses which employ a triphenylphosphonium salt as the starting compound and are used to prepare any olefin, ie. neither the nature of the above radicals $R^1$ to $R^3$ nor the nature of the acid radical $X^\ominus$ nor the nature of the base affects the applicability of the process. Hence, a detailed discussion of the reactants used in such syntheses is superfluous. We would merely record that the most important industrial application of the process is the syntheses of compounds of the carotinoid series, eg. vitamin A and β-carotene.

Accordingly, the ylid radicals $R^1$ are preferably aliphatic or cycloaliphatic-aliphatic polyenyl groups of 5 to 20 carbon atoms, especially 3-methyl-4-dimethoxy-but-2-en-1-yl, β-ionylidene-ethyl and axerophthyl:

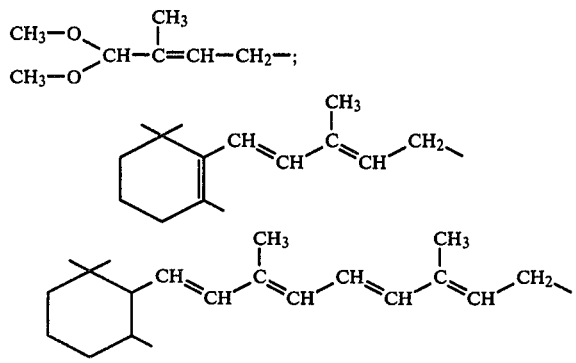

The acids conventionally used to form the phosphonium salt are sulfuric acid, nitric acid, HCl, HBr, acetic acid, formic acid, propionic acid, toluenesulfonic acids, oxalic acid, trichloroacetic acid and the acid salts of polybasic acids, eg. bisulfates and others.

However, all salts capable of forming triphenylphosphonium salts are applicable to the process according to the invention.

On the other hand, acids with relatively large organic radicals are less suitable, because the effluent should be as free as possible from organic constituents.

The carbonyl compounds employed in the synthesis are in the main aldehydes ($R^3$=H). The organic radicals $R^2$ may belong to the same category as the radicals $R^1$ or may contain a smaller number of carbon atoms. Frequently, these radicals carry functional groups, eg. hydroxyl which is free or esterified with a lower carboxylic acid. Examples of industrially particularly important carbonyl compounds are γ-acetoxytiglaldehyde, ethyl β-formylcrotonate, 2,7-dimethyl-octa-2,4,6-triene-1,8-dial, retinal, β-apo-12'-carotinal, β-apo-8'-carotinal and their homologs.

The bases most commonly used in the olefin synthesis are aqueous or anhydrous alkali metal hydroxides and alkaline earth metal hydroxides, and aqueous or anhydrous ammonia, the alkali metal carbonates and alkaline earth metal carbonates, preferably sodium carbonate and potassium carbonate, and basic magnesium carbonate and calcium carbonate. The use of KOH, NaOH, LiOH, Mg(OH)$_2$, Ca(OH)$_2$ or Ba(OH)$_2$ is particularly advantageous. It is true that organic amines, eg. dimethylamine or triethylamine, may also be used, but they only rarely offer advantages over the cheap bases. The use of organic amines is less desirable from the point of view of the treatment of the residues, since—if they are used—the effluent requires a special treatment because of its organic content and cannot be discarded directly.

The formation of the phosphonium salts and the subsequent ylid reaction are as a rule carried out in an inert organic solvent. If the solubility of the components permits, a cheap, easily recoverable solvent, eg. methanol, is preferred, particularly since the latter has proved most suitable for the subsequent stage of the extraction of triphenylphosphine oxide. However, other solvents, eg. ethanol, propanols, butanols, glycols, glycol ethers, tetrahydrofuran, dioxane and methylene chloride may also be used; some of these, for example methylene chloride, are removed by distillation prior to the extraction. If they do not interfere with the extraction, as is the case, for example, with ethanol or isopropanol, they can possibly be removed, together with the methanol, in the steam treatment step according to the invention.

Methanolic solutions have proved most advantageous for the extraction, since the desired end product, namely the olefin, can be isolated particularly simply from these.

The extractant used is preferably a non-polar low-boiling hydrocarbon, eg. heptane, hexane, pentane, octane or an isomer mixture of these. Cyclohexane, methylcyclohexane and aromatic hydrocarbons, eg. toluene, xylene and benzene, may also be employed. In the case of the conventional syntheses of the carotinoid series, for example the synthesis of vitamin A acetate, the composition of the residues is approximately the following:

| Methanol | 0–80% by weight |
| Triphenylphosphine oxide | 5–80% by weight |
| Salts (eg. Na$_2$SO$_4$) | 1–40% by weight |
| Organic by-products | 0.01–20% by weight |
| Water | 0–90% by weight |
| Solvent other than methanol | 0–80% by weight |

These values are not critical and vary from case to case. In special Wittig syntheses outside the carotinoid field, the composition of the residue solutions may differ substantially from the above values, but this has no significant influence on the process according to the invention.

To carry out the process according to the invention in practice, the methanol, with or without a further solvent, is first steam-stripped at 80°–200° C. (ie. under pressure in the case of temperatures above 100° C.), under conditions such that the methanol is approximately replaced by an equal volume of water, ie. condensed steam. The effect of this treatment is that on the one hand all organic solvents which can be distilled off under these conditions are distilled off completely whilst on the other hand the salts contained in the residue remain in solution. Of course, it is desirable to keep the amount of the aqueous phase as small as possible. The optimum amount of water for carrying out the process successfully can be readily determined from a few preliminary experiments. The requirement that the volume of water and of methanol should be approximately the same is thus merely given as a guideline.

After the steam treatment, in which all components of the residue are thoroughly mixed, and during which the phosphine oxide hydrate—a compound which plays an important role in the process but of which the exact chemical nature is not known—is formed, the mixture is transferred into a settling vessel, where two liquid phases form at 80°–100° C. It was surprising that two liquid phases should form, since, because of the high melting point of triphenylphosphine oxide, namely 156° C., crystallization would have been expected, which would have made a separation very difficult or even impossible. These two liquid phases are separated in the conventional manner and separately processed further. The aqueous saline phase is as a rule discarded unless it contains particularly valuable salts which warrant recovery. The organic content of the aqueous phase, namely 0–1%, is surprisingly low and hence hardly constitutes a load on the chemical-biological effluent treatment to which industrial effluent must be subjected.

The lower organic phase consists of 70–90% by weight of triphenylphosphine oxide, 4–6% by weight of water and 26–4% by weight of organic impurities from the olefin synthesis. It is surprising that the phase containing the triphenylphosphine oxide is such a powerful solvent for organic materials in spite of its high water content (50 mole %). Whether the organic phase is burnt or the triphenylphosphine oxide is recovered therefrom by distillation or recrystallization is a question of economics. As a rule, however, recovery will be worthwhile since the phosphorus compound can be reconverted to valuable triphenylphosphine. Only the residue which then remains is in most cases valueless and is therefore burnt or destroyed by other means.

The process according to the invention can be carried out batchwise or continuously, by the conventional methods, Since it does not entail any technical peculiarities, more detailed explanations are superfluous. The steam treatment according to the invention is carried out particularly advantageously in a column, at the top of which the mixture of methanol, water, triphenylphosphine oxide, salts and organic by-products is run in, whilst steam is passed in at the bottom.

Using the process according to the invention it is possible to free the effluent, from syntheses in which triphenylphosphine oxide is formed, in a simple manner from the latter compound and from other organic impurities, which on the one hand substantially facilitates clarifying the effluent and on the other hand provides a simple method of recovering the triphenylphosphine oxide. The latter, which is easily purified by distillation or recrystallization, can then be used, for example, for the preparation of triphenylphosphine, an essential reactant for Wittig syntheses, for the preparation of triphenylphosphine dichloride, required for the synthesis of pesticides, as a flame-retardant or as an extractant for organic materials. The latter use offers great advantages, since triphenylphosphine oxide is of low flammability, and, because of its high boiling point (380° C.) allows lower-boiling materials to be separated off easily.

EXAMPLE 1

The reaction of 562 g (1 mole) of β-ionylideneethyltriphenylphosphonium bisulfate in 1 liter of water with 180 g (1.27 moles) of γ-acetoxytiglaldehyde and an aqueous solution of 207 g of potassium carbonate, followed by working up the reaction batch with methanol and heptene, gave, in addition to the desired product vitamin A acetate, a residue of essentially the following composition:
- 1,850 g of water,
- 2,240 g of methanol,
- 278 g of triphenylphosphine oxide,
- 175 g of potassium sulfate
- 60–70 g of potassium carbonate and organic impurities.

Blowing 2.5–3 kg of steam into this residue resulted in the entire methanol being stripped off in the form of a mixture with water, containing about 50 percent by weight of methanol. The composition of the distillate obtained depends on the apparatus.

The residue left after the steam treatment separated into an upper, aqueous phase in which the inorganic salts were dissolved, and into an organic phase which was liquid above 80° C. and contained triphenylphosphine oxide together with the non-volatile organic by-products present in the original aqueous-methanolic extraction residue.

The aqueous phase contained about 175 g of potassium sulfate, 60–70 g of potassium carbonate and only traces of organic material in 2.6 kg of water and could therefore be passed to the effluent treatment process without presenting any problems.

The lower organic phase consisted of 300 g of an oil which, according to phosphorus analysis, approximately contained about 278 g of triphenylphosphine oxide and 22 g of substantially organic by-products. The triphenylphosphine oxide crystallizes below 80° C. and can, after purification, by employed for recovering triphenylphosphine by conventional processes.

EXAMPLE 2

1,582 Parts by weight of an olefin synthesis residue of approximately the following composition:
- 763 parts by weight of water,
- 571 parts by weight of methanol,
- 101 parts by weight of triphenylphosphine oxide,
- 123 parts by weight of inorganic salts,
- 120 parts by weight of organic by-products and
- 3 parts by weight of hydrogen peroxide were worked up in accordance with the invention.

For this purpose, 1,582 parts by weight per hour were charged into a packed column of appropriate size, which was directly heated with 871 parts by weight of steam per hour. The distillate obtained per hour consisted of a mixture of 568 parts of methanol and 571 parts of water.

The bottom product, which was at about 99° C., consisted of 1,313 parts by weight, per hour, of a two-phase mixture of approximately the following composition:
- 1,063 parts by weight of water
- 101 parts by weight of triphenylphosphine oxide,
- 123 parts by weight of salt,
- 20.5 parts by weight of organic impurity, and
- 3 parts by weight of methanol (~0.1%).

This hot bottom product was fed continuously into a heated separating vessel (phase separator). The upper phase which issued consisted of 1,179 parts, per hour, of a solution of 1,054 parts by weight of water, 122.5 parts by weight of inorganic salts, 1 part by weight of triphenylphosphine oxide, 0.5 part by weight of organic impurities and 1 part by weight of methanol. The lower phase which issued consisted of 129.6 parts by weight, per hour, of a mixture of 100 parts by weight of triphenylphosphine oxide, 7 parts by weight of water, 0.6 part by weight of inorganic salts, 20 parts by weight of organic impurities and 2 parts by weight of methanol, this mixture being liquid above 80° C. This phase can be used for conversion to triphenylphosphine.

We claim:
1. A process for the treatment of residues, consisting principally of methanol, triphenylphosphine oxide, salts and organic by-products, from the synthesis of olefins using triphenylphosphonium salts comprising
   (a) steam stripping the residues at from 80° to 200° C. to remove the volatile constituents, principally methanol,
   (b) the steam treatment being carried out in such a way that at least sufficient water to keep the salts, contained in the residue, in solution can condense in the residue, (c) transferring the aqueous organic mixture formed into a settling vessel, where it is kept at 80°-100° C. and (d) separating from one another the phases which form in the vessel, namely a saline aqueous solution and an organic solution containing principally triphenylphosphine oxide.

* * * * *